(12) United States Patent
Koch et al.

(10) Patent No.: US 7,021,936 B2
(45) Date of Patent: Apr. 4, 2006

(54) INTEGRAL GUTTA PERCHA CORE/CONE OBTURATION TECHNIQUE

(76) Inventors: Kenneth Koch, 23 Misty Meadow, Irvine, CA (US) 92612; Dennis Brave, P.O. Box 906, Brooklandville, MD (US) 21022

( * ) Notice: Subject to any disclaimer, the term of this patent is extended or adjusted under 35 U.S.C. 154(b) by 0 days.

(21) Appl. No.: 10/744,648

(22) Filed: Dec. 22, 2003

(65) Prior Publication Data
US 2004/0137404 A1    Jul. 15, 2004

Related U.S. Application Data

(60) Provisional application No. 60/436,793, filed on Dec. 27, 2002.

(51) Int. Cl.
*A61C 5/02* (2006.01)

(52) U.S. Cl. ............................................. 433/224

(58) Field of Classification Search ............... 433/102, 433/165, 224
See application file for complete search history.

(56) References Cited

U.S. PATENT DOCUMENTS

| | | | |
|---|---|---|---|
| 4,044,507 A | 8/1977 | Cox et al. | 51/424 |
| 4,449,938 A * | 5/1984 | Pollak | 523/116 |
| 4,657,592 A * | 4/1987 | Takubo | 106/35 |
| 4,951,366 A | 8/1990 | Geller | 26/28 |
| 5,104,322 A * | 4/1992 | You | 433/224 |
| 5,199,229 A | 4/1993 | Herold et al. | 51/439 |

(Continued)

OTHER PUBLICATIONS

Koch DMD; Ken "Comparison of apical leakage between Ketac Endo Sealer and Grossman sealer", oral surgery, oral medicine, oral pathology, vol. 78, No. 6, ©1994, pp. 784-787.

(Continued)

*Primary Examiner*—Cary E. O'Connor
(74) *Attorney, Agent, or Firm*—Alfred M. Walker; Lee Grosskreuz Hechtel (57) ABSTRACT

An integral, one-piece silanated particle impregnated gutta percha core/cone technique employs a thin layer of a luting agent, such as glass ionomer cement with a machined gutta percha core/cone, precisely matches the preparation, thereby reducing leakage and achieving a hermetic seal. The hermetic seal is further enhanced by a mono-block bond that occurs between the silanated particles in the gutta percha and the appropriate chemical sealant. Optional cryogenic treatment of the gutta percha material changes its molecular weight, making it stiffer and conducive to forming an integral, one piece core/cone, without the need for a separate carrier core to install the tapered gutta percha core/cone within the root canal. Additionally, the tapered body of the core/cone may be reticulated in a slightly three dimensional texturized framework to increase surface area and therefore increase retention. Optional line demarcation indicia are also placed on the core/cone. Additionally, the head of the core/cone can be gripped by a delivery vehicle clasp.

103 Claims, 10 Drawing Sheets

U.S. PATENT DOCUMENTS

| | | |
|---|---|---|
| 5,275,562 A | 1/1994 | McSpadden ................ 433/224 |
| 5,769,638 A | 6/1998 | Torabinejad et al. ..... 433/228.1 |
| 5,842,861 A | 12/1998 | Buchanan ................... 433/102 |
| 6,053,735 A | 4/2000 | Buchanan ................... 433/224 |
| 6,261,099 B1 | 7/2001 | Senia et al. ................. 433/224 |
| 6,264,471 B1 | 7/2001 | Martin ....................... 433/224 |
| 6,371,764 B1 | 4/2002 | Brave ......................... 433/224 |
| 6,428,319 B1* | 8/2002 | Lopez et al. ................ 433/224 |
| 6,513,254 B1* | 2/2003 | Lunn ............................ 33/513 |
| 2000/0123024 | 9/2002 | Jensen et al. ............... 433/224 |
| 2003/0148247 A1* | 8/2003 | Sicurelli et al. ............ 433/220 |
| 2003/0199605 A1* | 10/2003 | Fischer ....................... 523/116 |
| 2003/0219699 A1 | 11/2003 | Martin ....................... 433/164 |

OTHER PUBLICATIONS

"Endo-eze with AET" Ultradent Corp., illustrated Technique guide, 17 pages, 2001.

PCT Search Report, PCT/US03/41236, Applicant: Kenneth Koch et al., dated May 27, 2004, 6 pages.

* cited by examiner

INTEGRAL GUTTA PERCHA CORE/CONE OBTURATION TECHNIQUE

RELATED APPLICATIONS

This application claims benefit 35 USC (119(e) from provisional patent application serial No. 60/436,793, filed Dec. 27, 2002.

FIELD OF THE INVENTION

The present invention relates to Endodontics and, more specifically, the obturation (or the creation of a root canal seal by the use of a sealing material into the tight tapered apical end of a root canal) of the root canal space in a tooth.

BACKGROUND

Historically, there have been a number of ways to fill or obturate a root canal space. After a tooth has been thoroughly shaped and debrided of diseased nerve tissue, a filling of the space is required to prevent the ingress of contaminants from both the top section of the root canal (coronal) and the bottom portion (apical). The goal is a hermetic seal of the root canal system. The most common cause of failure of root canals is bacterial contamination either through microleakage or contamination during the process. The better the seal can be accomplished, the greater the long term prognosis of the tooth.

Initially silver points were used to fill the canal space, but due to leakage problems associated with their shape and the material itself, this technique was abandoned. This was replaced with the cold lateral filling by forcible condensation of gutta percha points.

Gutta percha is a naturally occurring trans isomer of rubber itself that can be modified into points. Gutta percha is typically formulated into a tapered conical shape (such as a 0.02 taper) to assume the tapered conical shape of the apical end of the root canal of a tooth. Because it is malleable, gutta percha at times has been inserted as an obturator. An obturator is a pointed instrument having a tapered distal end core and a cylindrical handle at the other end. The malleable gutta percha is wrapped around the tapered distal end core of the obturator instrument, and the handle is grasped manually. However, grasping the obturator manually often obstructs the view of the delivery process of the obturator into the root canal site.

Using a separate tapered carrier core for introducing gutta percha wrapped around it often results in uneven dislodging or stripping of the heated gutta percha from the obturator instrument.

Therefore, there is a need for an integral one piece gutta percha core/cone of the present invention, which acts as its own carrier, which can strongly bond to a thin layer of cement coating the inner walls of a root canal. This gutta percha core/cone of the present invention is used at ambient room temperature, (not heated), and therefore is not subject to stripping or shrinkage.

Depending upon the commercial brand, gutta percha cones contain 18–23% pure gutta percha. Waxes, resins, fillers, zinc oxide, and barium sulfate comprise the remainder of the filling material (cones) known by the colloquial trade name of "gutta percha".

The cold lateral condensation filling technique employs a series of sequentially intertwined gutta percha cones placed in a sea of cement. The cement formula originally was a zinc oxide eugenol cement. Although popular, this technique was subject to voids as a result of the lateral condensation filling and inaccuracies of adaptation to the root canal wall. It is very difficult with lateral condensation filling to achieve a three dimensional seal of the root canal system.

The next change in the condensation filling process was the introduction of thermoplastic techniques that heated the gutta percha with hand instruments before insertion of the gutta percha into the apical end of the root canal. The rationale behind thermoplastic gutta percha is that heated gutta percha flows and will more readily adapt to irregularities in the root canal system. Unfortunately, heated gutta percha flows only a few millimeters and shrinks upon cooling, thereby not filling the root canal space it was intended to fill and seal. Consequently, the use of a luting agent is recommended with all thermoplastic techniques. While seemingly attractive, heated gutta percha has its limitations. Shrinkage upon cooling and being technique sensitive are two of the limitations.

A further development in the obturation process was the introduction of alpha phase gutta percha inside the root canal on a carrier (plastic or metal). The combination of gutta percha on a carrier was referred to as an obturator. The success of this technique had the limitation of being dictated by the success of the preparation. If the taper of the preparation was not sufficient, the tooth structure could strip (denude) the gutta percha from the carrier, thereby reducing the success of the technique. A carrier that has a portion stripped of gutta percha increases the risk of bacterial contamination and therefore reduces the prognosis.

Recently, Endodontics has been witness to numerous heated gutta percha techniques that all have the common problem of shrinkage. Additionally, some of these techniques are technically sensitive making the use of thermoplastic techniques particularly challenging for the general practitioner.

There also was the concept of filling the entire root canal with a cement or paste, not utilizing gutta percha. This method had numerous problems such as lack of control of the material, and serious shrinkage that resulted in leakage and bacteria contamination. Revisement challenges were also a factor if the root canal procedure had to be re-treated.

Additionally, more recently, the concept of a single cone of gutta percha used with a large amount of cement has been advocated by Ultradent Incorporation with their ENDO-EZE® technique and its related Anatomic Endodontic Technology (AET)™ technique, using their ENDO-REZ® resin sealer.

However, the lack of synchronicity between the root canal preparation and the cone is a problem, as well as the cements, which do not adapt and bond well to the walls of the preparation or to the gutta percha itself. With the use of the Ultra Dent ENDO-EZE® preparation and the AET™ technique with the ENDO-REZ® resin sealer, there is inconsistency between the root canal preparation and the gutta percha used to fill the root canal space. Therefore, the lack of a precise match between the preparation and the gutta percha itself results in either excess cement (that will shrink) or the gutta percha cone can hang up in the coronal part of the canal and therefore, not reach the end of the root canal preparation intended to be sealed by the gutta percha. This can result in leakage and bacterial contamination thereby reducing the prognosis of the case.

However, Koch et al. and others, showed in 1993 that glass ionomer cement in its original formulation offered promise as a single cone cement to hold the gutta percha seal in place within the root canal. Other authors still expressed concern with the bond of the glass ionomer cement to the gutta percha. In other words, while the bond of the glass ionomer to dentin was superior to other sealers, the bond to gutta percha was merely adequate. Another concern is the real probability that the large amount of cement in a single cone technique, as a thick layer of cement, will shrink more than a thin layer of cement. This potential problem is the result of a lack of synchronicity between the root canal preparation and the gutta percha cone. As an example, one cannot place a 0.02 taper gutta percha cone into a 0.04 taper preparation and expect good results. The cone must match the tapered and/or curved shape preparation of the root canal in as precise a manner as possible.

Furthermore, the restoration of endodontically treated teeth has been subject to a lack of synchronicity between the root canal preparation and a prefabricated post. The consequence of this disparity is less than ideal retention of the post, as well as a weakening of the root when posts of greater dimension, or different shapes, are utilized, thereby compromising the long-term success of the restoration and the tooth.

An additional concern of the restoration of endodontically treated teeth is the lack of a proper coronal seal. The lack of a three dimensional seal (on top of the gutta percha in the root canal) can result in an ingress of bacterial components. Bacterial contamination will result in failure of the root canal and remains a serious concern in modern endodontics.

OBJECT OF THE INVENTION

It is therefore the object of this invention to introduce the concept of synchronicity between the gutta percha core/cone and a machined preparation of a root canal wherein the gutta percha core/cone precisely matches the machined root canal preparation. Consequently, the matching gutta percha core/cone in combination with a next generation glass ionomer cement reduces leakage and achieves a hermetic seal of the root canal. There are properties and designs unique to both the cement and gutta percha that distinguish this technique from any previous methodology. Additionally the gutta percha core/cone is delivered to the tooth (inserted) by use of a "TRANSPORTERS"™ delivery vehicle facilitating its use in the endodontic procedure.

An additional object of this invention is to have a post system that precisely matches the endodontic preparation, thereby insuring the success of the post and the associated restoration.

A further object of this invention is to have a system (kit) that establishes a plug on top of the root canal, thereby insuring the seal of the said root canal.

SUMMARY OF THE INVENTION

In keeping with these objects and others which may become apparent, this invention takes a basic gutta percha cone and transforms it into a gutta percha core/cone, that functions as both the tapered filling cone and as its own carrier core. By optionally changing the molecular weight of a substance, such as gutta percha, one can change the properties of this material. The molecular weight of this gutta percha has been altered to produce a stiffer cone, which acts as its own structural core. Without the need for a separate interior carrier of plastic or metal, the gutta percha core/cone will occupy the entire space of the prepared root canal, with the exception of a microthin layer of luting agent between itself and the dentinal wall of the tooth. Additionally, the apical 16 mm of the core is preferably reticulated in a texture, such as a lattice (slightly three dimensional) framework to increase the surface area and thereby increase retention. Besides being a lattice, texturization may assume other surface interruption configurations, such as dimpling, stippling, irregular or parallel marking, etc. A further option for reticulation is the use of sand blasting, employing a granular substance, such as aluminum oxide.

Optional line demarcation lengths, in millimeters, are also placed on the core/cone. These line demarcations may preferably alternate between thick and thin or vary numerically. As an example, thick lines may designate odd numbers and the thin lines may designate even lines, or vice versa.

Additionally, the head of the core/cone has been shaped to accommodate the gripping portion of the TRANSPORTER™ delivery vehicle, such as disclosed in U.S. Pat. No. 6,371,764 of Applicant Dennis Brave, dated Apr. 16, 2002, for a dental instrument for placing gutta percha carried by an obturator into a root canal. In Brave '764, a clasp at the end of an elongated hand held handle of the obturator grasps the upper cylindrical handle of an obturator core carrying gutta percha. In the present invention, the clasp grips the proximal end of the single piece core/cone of gutta percha for insertion into the root canal.

This will facilitate placement of the core/cone into the root canal.

Lastly, the gutta percha has been preferably optionally subject to cryogenic freezing treatment, thereby slightly increasing the surface area of the core/cone and increasing its retention to a glass ionomer cement. The molecular structure of the gutta percha has also been altered by the cryogenic treatment to allow a more intimate contact between the glass ionomer cement and the gutta percha core. The cryogenic treatment additionally adds further rigidity to the gutta percha core/cone making it easier to place in curved canals.

Adding to the system concept of this invention, the gutta percha core/cone is preferably independently packaged in a seal thereby assuring asepsis and reducing the potential for bacterial contamination.

Another concept of this single core/cone system is the option of having different cements to act as a luting agent. Siloxanes, such as polymethylvinyl siloxanes, as well as methacrylates, and other resin based cements will all work with this technique. The previously listed cements, epoxy resins and glass ionomers will also meet the requirements of this technique. For example, synthetic or chemically modified naturally occurring resin sealers may be used. One preferable version of this invention uses a second generation glass ionomer cement that contains properties that ensure a definitive bond to the dentin and an intimacy with the gutta percha core/cone. This particular cement additionally may contain a zinc component that adds to the antibacterial effect of this luting agent (acting as a sealer).

In summary, the present invention includes an endodontic integral one-piece gutta percha core/cone, which, in combination with an appropriate luting agent properly seals, in a three dimensional manner, a root canal preparation space. Lateral canals can be more effectively filled with sealers that exhibit little or no shrinkage, rather than thermoplastic obturation techniques that produce shrinkage upon cooling. Additionally there are sealers also available in endodontics, such as methylacrylates, that in fact expand slightly rather than shrink, which can fill lateral canals of a root canal more successfully than thermoplastic gutta percha.

The gutta percha core/cone includes a handle portion adapted to be gripped by a hand or a delivery vehicle clasp. A length determination section adjoins the handle portion with depth markings to indicate when the endodontic integral one piece core/cone is fully inserted into a root canal. The main body of the core/cone includes a conical section adjacent to the length determination section.

The tapered conical section is preferably reticulated to increase the surface area and is inserted into the root canal with a cement, such as a glass ionomer, which coats the surface area of the conical section. Reticulation may take any form of texturization, such as, for example, cross hatching with intersecting longitudinally extending protrusions and recesses, or it may be in other forms, such as a plurality of individually protruding bumps, recessed dimples, or sand blasting with a substance such as aluminum oxide.

Optionally the gutta percha core/cone is cryogenically deep frozen, which increases bonding to the surface area of the tapered cone.

The endodontic integral one piece gutta percha core/cone is preferably packaged in a seal.

The core/cones may be provided in a set of core/cones with constant tip size and variable tapers, or with variable tip sizes and constant taper.

The post system that matches the core/cone is designed to fit a fully tapered 0.06 taper preparation with specific sizing. The post includes an intra-radicular section and a "head" component that is coronal to the root canal orifice. This post may be fabricated from any of the common post materials, such as stainless steel, titanium, titanium alloys, fiber components or ceramics.

Creation of a three dimensional coronal seal is a further object of this invention. This can be created through the combination of a self-limiting drill (in multiple sizes) and an associated filling material, such as glass ionomer or a resin filler.

BRIEF DESCRIPTION OF THE DRAWINGS

The present invention can best be understood in connection with the accompanying drawings, in which:

FIG. 5 also shows that the handle thereof is precisely machined to fit-the clasp of the core/cone TRANSPORTER™ delivery vehicle clasp as shown in FIG. 5B;

DETAILED DESCRIPTION OF THE INVENTION

As shown in the drawing FIGS. 1–9, the integral, one piece gutta percha core/cone 10 has three distinct structural components all produced from the same material, such as gutta percha.

Figure 5:
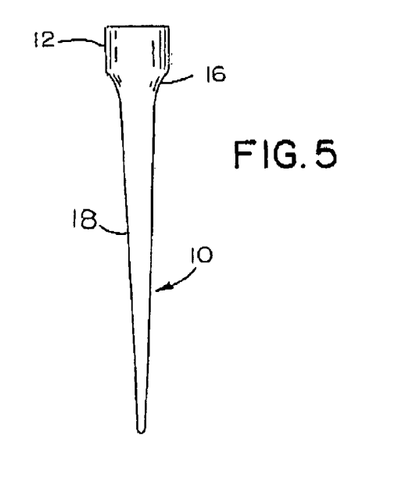
FIG. 5 is a side elevational view showing the contiguous handle of the gutta percha core/cone of the present invention that is comprised of the same material as entire core/cone itself.
Figure 5A:
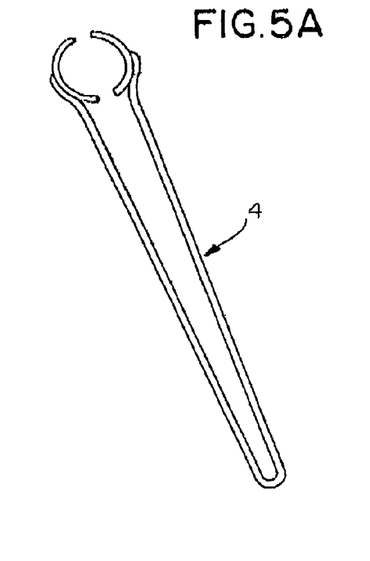
FIG. 5A is a view showing the core/cone TRANSPORTER™ delivery vehicle clasp alongside the handle of the gutta percha core/cone of the present invention shown in FIG. 5.
Figures 5B, 6:
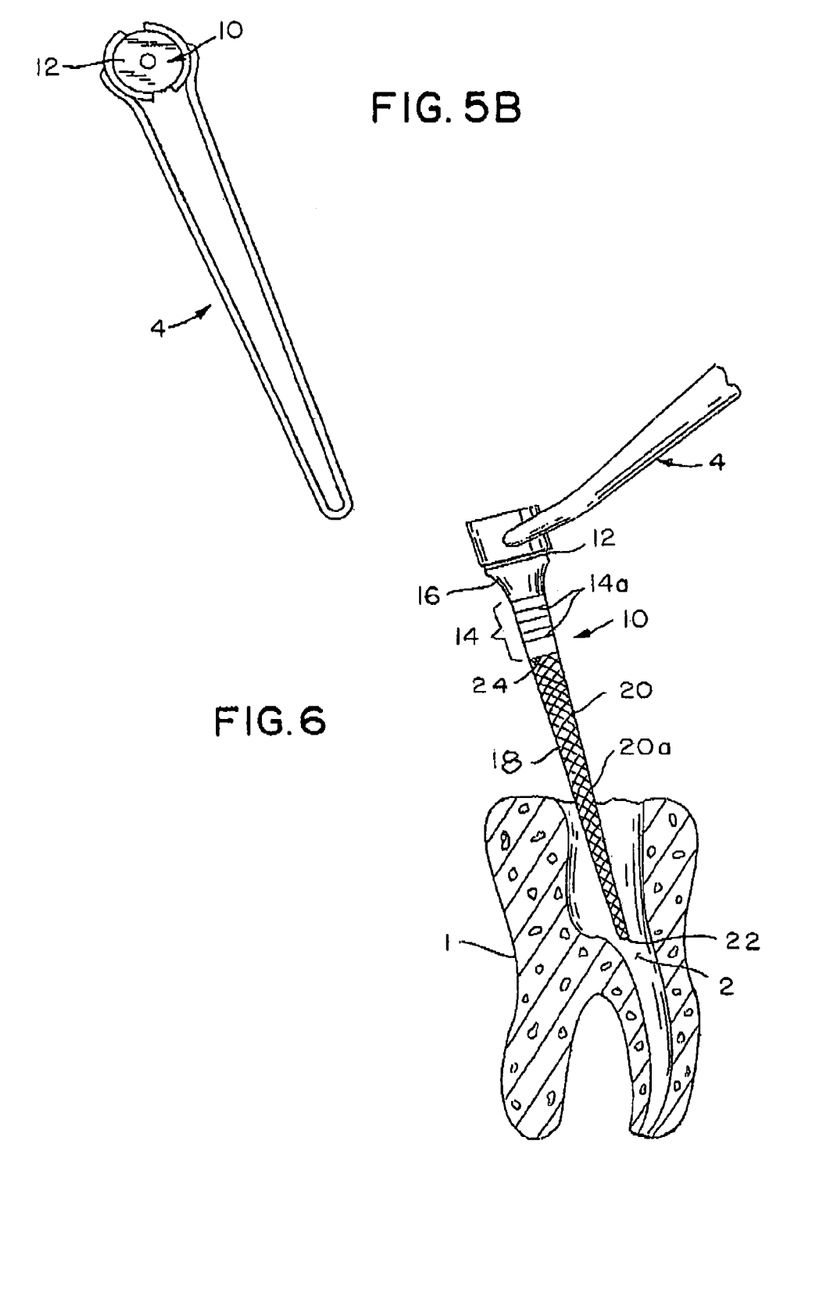
FIG. 5B is a top plan view showing the core/cone TRANSPORTER™ delivery vehicle clasp securely holding in place the gutta percha core/cone of the present invention.
FIG. 6 is a side elevational view in partial sagital crossection showing the core/cone TRANSPORTER™ delivery vehicle holding the core/cone of the present invention in its grip and inserting the core/cone into the orifice of the prepared root canal.

The top (proximal end) of the core/cone 10 comprises the handle section 12. The handle 12 is machined to. precisely fit the core/cone TRANSPORTER™ delivery vehicle 4 as shown in FIG. 5B. This precise fit prevents the handle 12, and therefore the core/cone 10, from rotating or shifting when taken to and inserted into the root canal 2 of the prepared tooth 1.

Core/cone 10 is inserted within root canal 2 so as to seal the entire portion below its upper orifice 2a, above which includes upper chamber 2a of tooth 1, which is filled with tooth colored resin and related crown post work (not shown).

The handle 12 allows the TRANSPORTER™ delivery vehicle 4 to perform its functions, among which is to facilitate the placement of the one piece integral gutta percha core/cone 10 into a root canal 2 of a tooth 1 without danger of mis-insertion.

Figure 1:
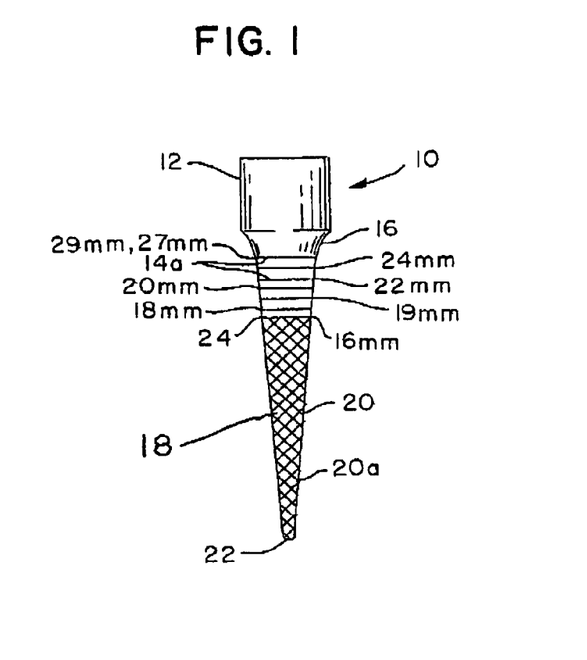
FIG. 1 shows a front elevational view of the conically shaped gutta percha core/cone of the present invention, including the top, widest cylindrical handle portion, the next level of optional line markings and the lower tapered reticulated intra canal portion.
Figure 1A:
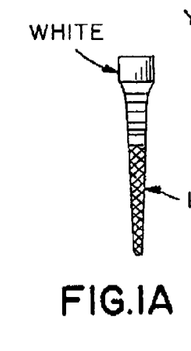
FIGS. 1A, 1B, 1C, 1D, 1E and 1F show a set of six gutta percha core/cones of the present invention, each individually marked according to optional ISO coordinated color markings on the top and side surfaces of the handle of each of the respective gutta percha core/cones.
Figures 1B, 1C, 1D, 1E:
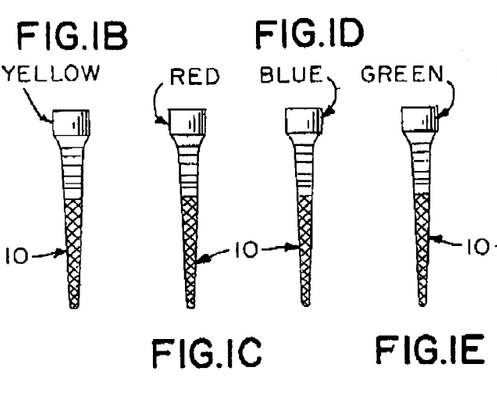
Figure 1F:
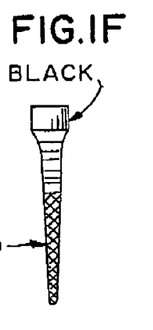
Figure 2:
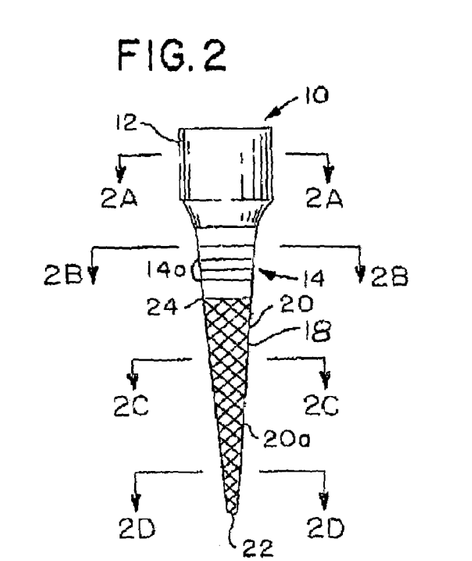
FIG. 2 shows a side view of the gutta percha core/cone of the present invention, which is a mirror image of the front view shown in FIG. 1, demonstrating the consistency in shape of the handle, length (depth) area, and the tapered intracanal portion.
Figure 2A:
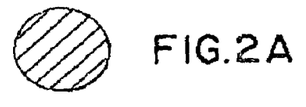
FIGS. 2A, 2B, 2C and 2D show horizontal sagital crossectional views of the gutta percha core/cone of the present invention as in FIG. 2, taken along respective directional arrow lines "2A—2A", "2B—2B", "2C—2C" and "2D—2D" of FIG. 2, showing the decreasing diameter of the gutta percha core/cone from the top coronal end to the bottom apical tip thereof.
Figure 2B:
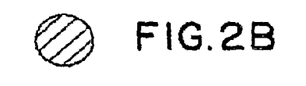
Figure 2C:
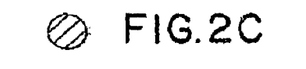
Figure 2D:
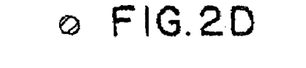
Figure 3:
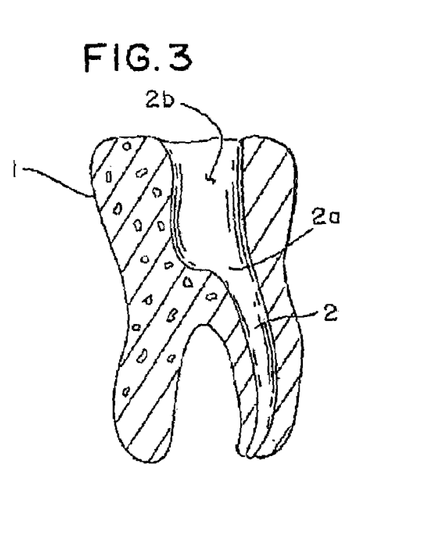
FIG. 3 displays a sagital, partial crossectional view of a fully tapered 0.06 root canal preparation ready for insertion of a gutta percha core/cone seal of the present invention therein.
Figure 3A:
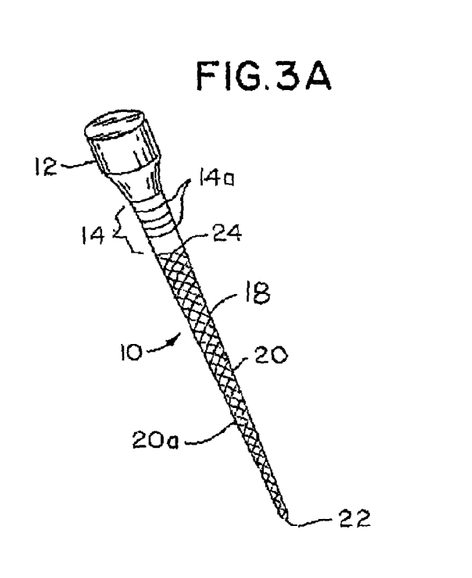
FIG. 3A displays a perspective view of the matching gutta percha core/cone of the present invention at the identical length from the end of the root canal as in FIG. 3.
Figures 4, 5C:
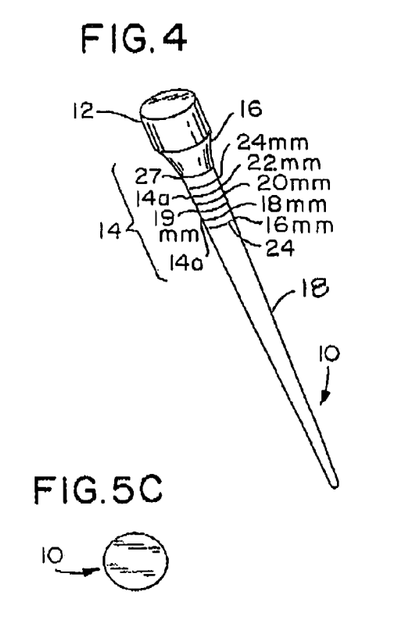
FIG. 4 is a perspective view showing the length determination markings on the gutta percha core/cone of the present invention, demarcating lengths preferably from 16 to 27 mm.
FIG. 5C is a top plan view of the core/cone of the present invention shown in FIG. 5.
Figure 4A:
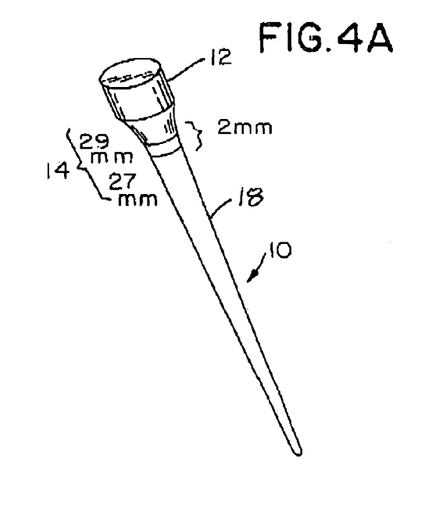
FIG. 4A is a perspective view displaying an additional 2 mm in length that can be determined from the beveled shoulder on the cylindrical handle portion attached to the top of the tapered body of the gutta percha core/cone of the present invention.

The optional but preferable length determination section 14 (with depth markings 14a) is another component of the gutta percha core/cone 10 and this segment of depth markings 14a has preferably measuring indicia, such as, for example, thick lines which denote odd lengths and thin lines which denote even numbered lengths, or vice versa. The lengths range from 16 mm at the first thick line 14 and extend to 27 mm at the last thick line 14a abutting the handle portion 12 of the core/cone 10. An additional 2 mm's may be gained by visually extending the indicia markings 14a proximally up until the beveled shoulder portion 16 of the cylindrical handle 12 at the proximal end of the conically shaped cone portion 18 of the core/cone 10 of the present invention.

A third segment of the gutta percha core/cone is the reticulated framework 20 extending from the most distal portion (distal apical tip 22 of core/cone 10), to the 16 mm line demarcation point 24. This reticulated framework 20 of varying optional texturizations 20a, is the portion of the core/cone 10 that is generally in the root canal 2 itself and its surface has been reticulated to increase the surface area, thereby increasing the retention of a luting agent sealer 8, such as preferably glass ionomer cement, to the core/cone 10.

Figure 8:
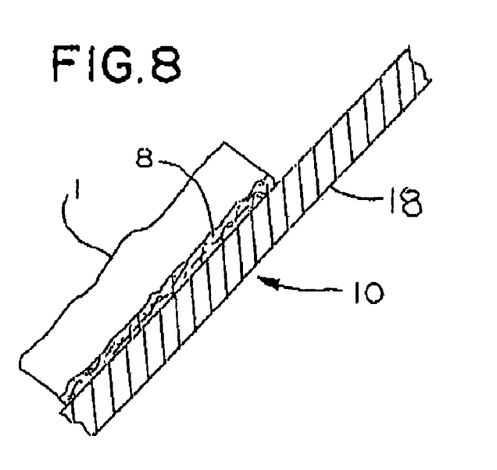

In connection therewith, as shown in the simulated scanning electron microscope (SEM) depiction of FIG. 8, the luting agent 8 is preferably applied in a microthin layer between the outside of the tapered portion of core/cone 10, and the dentinal material defining the tooth canal space. For example, the luting agent 8 is typically applied to fill the space, which is typically about from, but not limited to, about 0.01 mm to about 1.0 mm, with the exception of naturally occurring anatomical irregularities deviating from these dimensions, which are also filled by the luting agent 8.

Further adhesion is gained from the cryogenic treatment of the gutta percha core/cone 10.

The TRANSPORTER™ delivery vehicle 4 is a holding device that facilitates the precise insertion of the core/cone 10 into the root canal 2. In addition to contributing increased accuracy to the procedure, the TRANSPORTER™ delivery vehicle 4 helps the clinician insert the gutta percha core/cone 10 into the root canal 2 of all teeth without the fear of misdirection and consequential stripping of the luting agent sealer 8, such as cement, from the core/cone 10.

Another optional but preferable unique feature of this system is the cryogenic treatment of the gutta percha used to fabricate the core/cone 10. By a deep freezing process, the cryogenic treatment adds stiffness to the gutta percha and increases the surface area of the gutta percha core/cone 10, thereby resulting in a more intimate contact between the luting agent sealer 8 (such as glass ionomer cement) and the core/cone 10 itself. The result is increased retention.

Cryogenics changes the molecular structure of compounds to a martensite state rather than a retained austenite state. Therefore, coatings, such as luting agent sealers 8, have a greater affinity for martensite state rather than the austenite state. This results in a greater bond of the gutta percha core/cone 10 to the luting agent sealer 8.

The clinical application of this technique involves the creation of a machined fully tapered 0.03 to 0.08 preparation, preferably a 0.04 or 0.06 preparation in a root canal space 2. A machine preparation is achieved through the use of a rotary file sequence that prepares the canal in a predictable and consistent manner that produces a fully tapered preparation (0.03–0.08 mm). Examples of files that produce a fully tapered preparation are the PROFILE by Dentsply Tulsa Dental and the K-3 by SybronEndo. Following full instrumentation and debridement, the appropriate size gutta percha core/cone 10 is selected. As an example, if the final preparation is a machined, fully tapered 0.06 preparation, with an apical tip size of "20" (ISO), then a "20/0.06" gutta percha core/cone is selected. Following core/cone selection, an appropriate luting agent sealer 8, such as cement, is mixed (glass ionomer) and inserted into the root canal 2, creating a thin layer of luting agent sealer (cement) 8. The selected gutta percha core/cone 10 is then partially exposed in its sealed package 6 and is grabbed by the TRANSPORTER™ delivery vehicle 4. It is then fully removed by the TRANSPORTER™ delivery vehicle 4 from the sterile package maintaining asepsis. The chosen luting agent (root canal sealer 8), is then also placed on the gutta percha core/cone 10 itself, particularly over the reticulated area 20 of the core/cone 10 (apical 16 mm). It is recommended that gutta percha core/cone 10 be coated with the sealer 8 (cement) by wiping it gently through the mixed sealer 8.

The gutta percha core/cone 10 is now taken to the tooth and inserted into the prepared root canal 2 as far as the appropriate depth marking. After a few minutes, the lower tapered portion of the cemented gutta percha core/cone 10 is severed from the cylindrical handle 12 and length marking section 14, at the point of the orifice 2a of the canal 2 with a heated instrument, and subsequent light vertical condensation pressure is applied to the gutta percha core/cone 10.

Figures 6A, 6B:
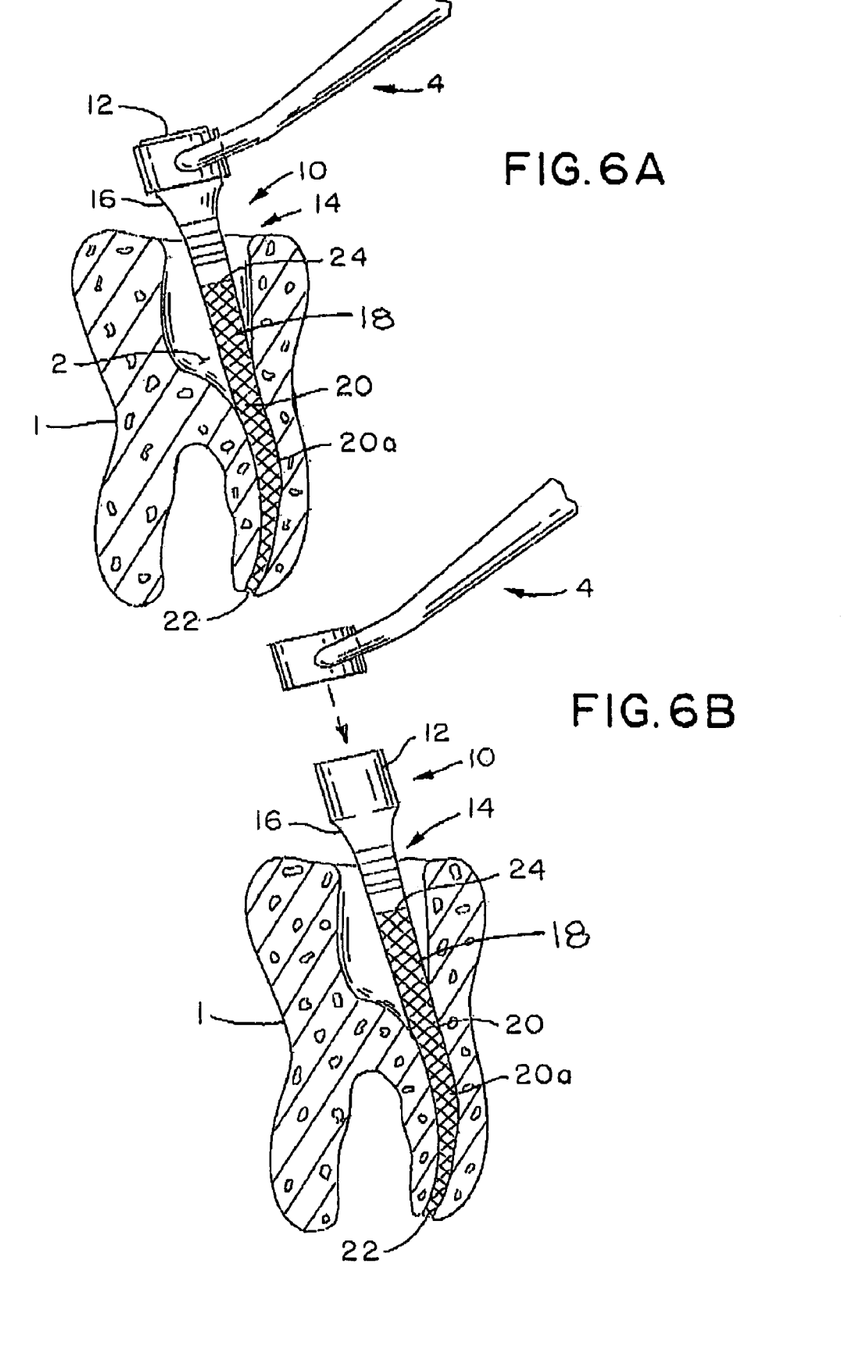
FIG. 6A is a side elevational view in partial sagital crossection showing the core/cone TRANSPORTER™ delivery vehicle clasp having placed the gutta percha core/cone of the present invention into the prepared root canal.
FIG. 6B is a side elevational view in partial sagital crossection showing the TRANSPORTER™ delivery vehicle clasp having released its grip on the gutta percha core/cone of the present invention and being removed from the field of treatment.
Figure 6C:
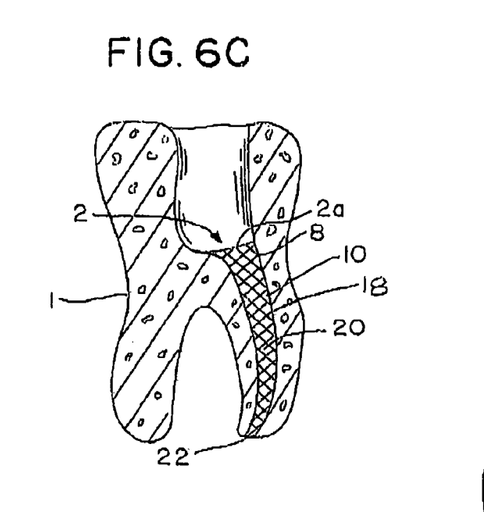
FIG. 6C is a side elevational view in partial sagital crossection showing the handle and top portion having been seared and cut off of the gutta percha core/cone of the present invention; leaving the lower portion thereof sealed within the root canal preparation.
Figure 6D:
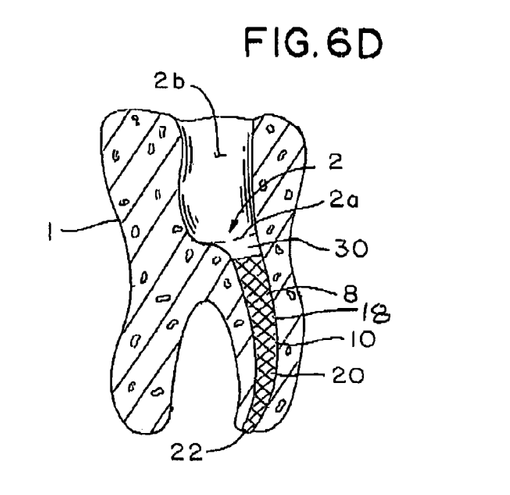
FIG. 6D is a side elevational view in partial sagital crossection of an alternate embodiment showing the handle and top portion having been seared and cut off of the gutta percha core/cone of the present invention, leaving the lower portion thereof sealed within the root canal preparation, wherein a prepared space is machined in the coronal aspect of the filled root canal, to thereafter be occupied and covered by a bonded restorative material on top of the filled root canal space.
Figure 6E:
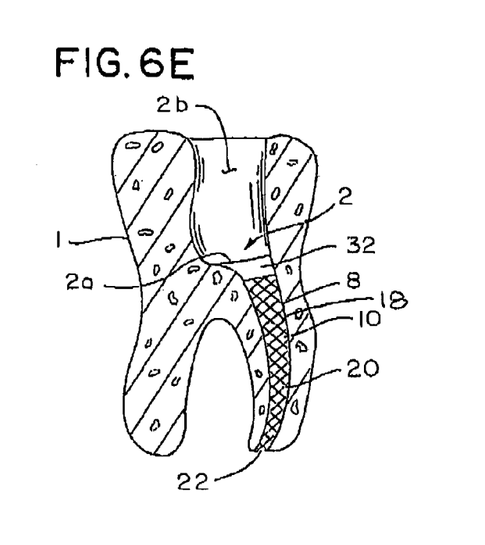
FIG. 6E is a side elevational view in partial sagital crossection of the alternate embodiment as in FIG. 6D, showing the aforementioned machined prepared space in the coronal aspect of the filled root canal having thereafter been occupied and covered by the bonded restorative material on top of the filled root canal space.

FIGS. 6D and 6E show an alternate embodiment for a coronal seal that can be further assured by the placement of a cover 32 of bonded restorative material, such as the Applicant's "ENDO-KAP™" or "ENDO-SEAL™", which is any dental restorative material, such as glass ionomer or a bonded resin, placed into a prepared segment recess 30 created by the removal of gutta percha core/cone material from the coronal aspect on top of the filled root canal space occupied by the severed gutta percha core/cone 10. This will prevent leaking and bacterial contamination of the coronal aspect of the root canal filling and further prevent the need for retreatment, due to secondary bacterial invasion.

Figure 6F:
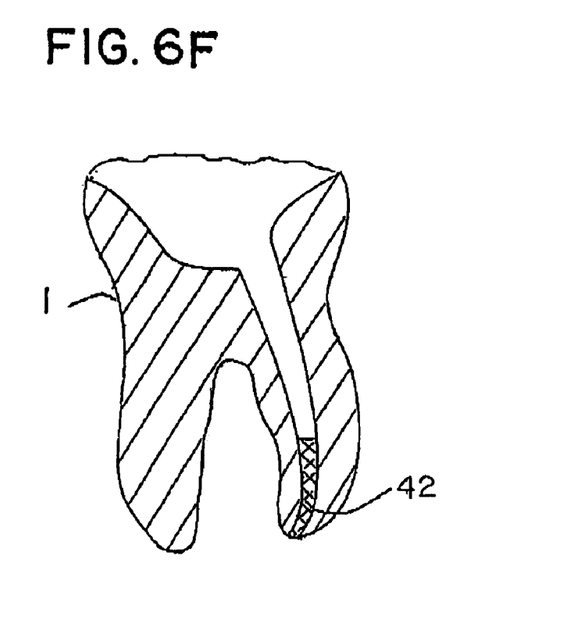
FIG. 6F is a side elevational view in partial sagital crossection of a further alternate embodiment, showing a machined prepared space in a tooth that requires a post/core for proper restoration.
Figure 6G:
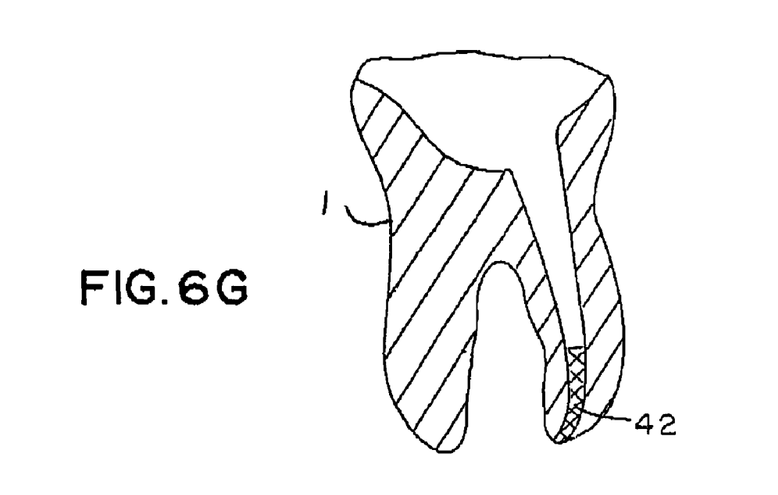
FIG. 6G is a side elevational view in partial sagital crossection of the further alternate embodiment as in FIG. 6F, showing the post accommodating space of the root canal having been refined to remove any surface irregularities that would inhibit full insertion of the post therein.
Figure 6H:
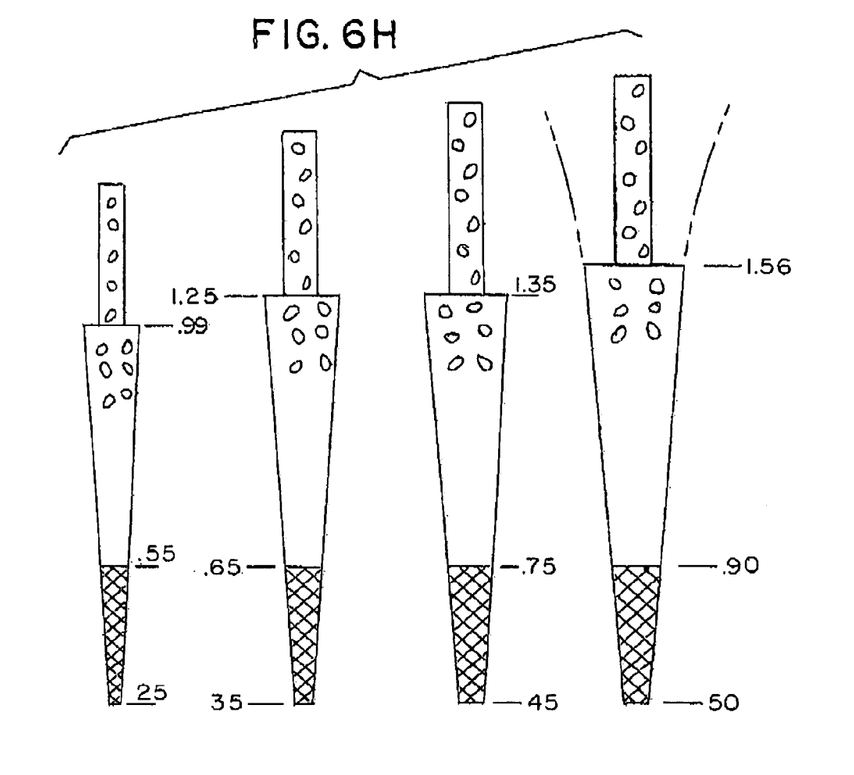
FIG. 6H is a side elevational view of the post to be inserted in the further alternate embodiment as in FIG. 6G, wherein a beveled portion is shown in phantom lines.
Figure 6J:
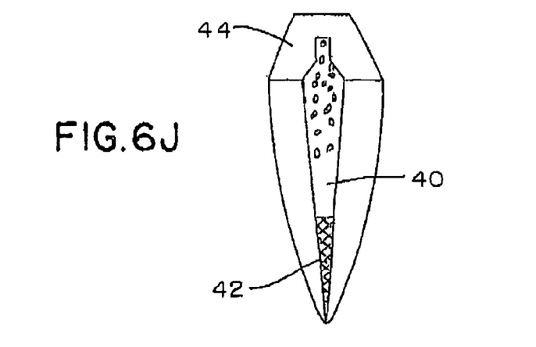
FIG. 6J is a side elevational view of the post as in FIG. 6H, shown inserted and modified to create the beveled head portion, that acts as a retentive device for the core buildup in the restored tooth.
Figure 7:
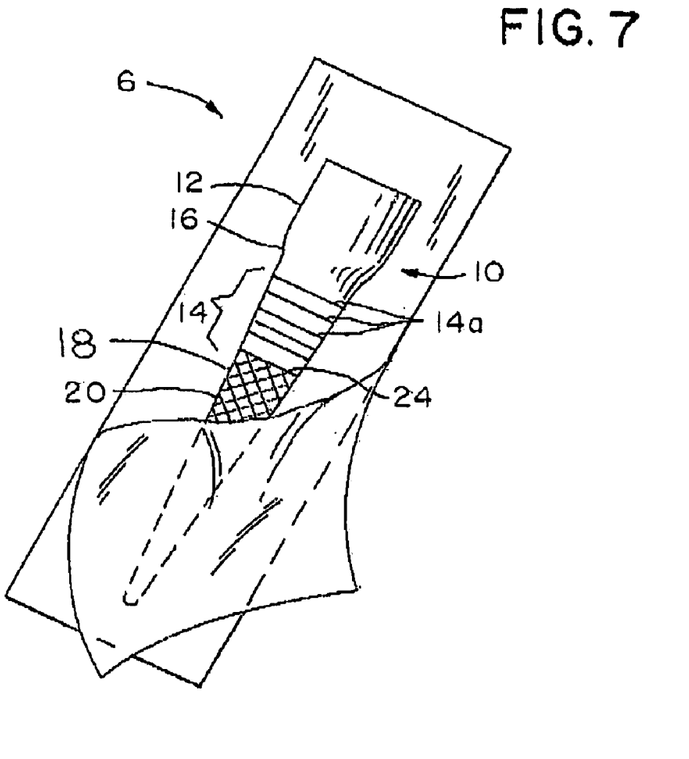
FIG. 7 shows the packaging of the gutta percha core/cone of the present invention in an individual sealed sterile package, shown partially torn open, exposing the gutta percha core/cone; and, FIG. 8 is a simulated scanning electron microscope (SEM) crossectional view of a microscopic portion of the present invention, showing a monolith effect of the synchronicity between the tooth (such as its dentin), the luting agent (such as glass ionomer cement) and the cryogenic treated gutta percha core/cone of the present invention.

Furthermore, in those cases where a post/core is required for a satisfactory restoration of a further tooth 1 shown in FIG. 6F, this invention includes a post system with post 40, as shown in FIG. 6H, that matches the fully tapered endodontic preparation of root canal 2 of tooth 1, so that synchronicity is maintained (for example, a 0.06 tapered post matches a 0.06 tapered endodontic preparation) between the preparation of root canal 2 and the post 40. There remains in the root canal 2, below the post 40, a variable section 42 of gutta percha, which is located apical to the post 40, that insures an apical seal and prevents contamination from the apical portion of the tooth 1. The fully tapered post 40 is cemented with a luting agent such as a glass ionomer or a resin-based sealer and the coronal section of the post 40 in FIG. 6H is covered with a coronal buildup material 44. The resulting post/core restoration of post 40 and core buildup 44, as shown in FIG. GJ, insures proper retention of the crown and also acts as an alternative coronal seal to microleakage.

A further option is to have a planing instrument, in those cases with significant surface irregularities, such as the curvature in the root canal of FIG. 6F, to refine the preparation, such as a 0.06 preparation, for example, in such a manner as to accommodate the tapered inflexible post 40, such as shown in FIG. 6G and thereby validate or verify the synchronicity between the preparation of the root canal 4 and the cemented post 40.

Figure 9:
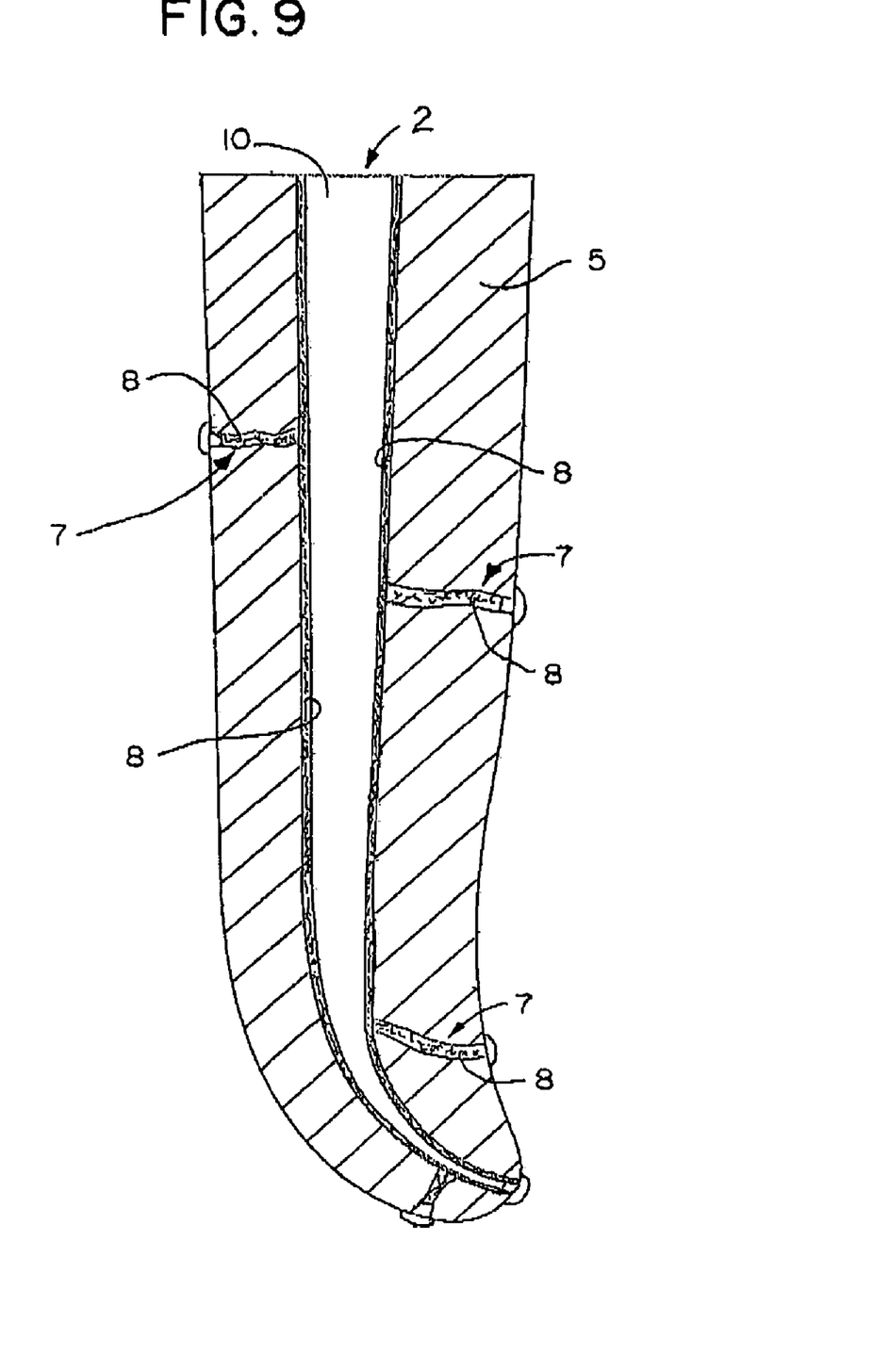
FIG. 9 is a side crossectional view of a tooth showing multiple lateral canals obturated with sealer following insertion of the core/cone.

As shown in FIG. 9, endodontic integral one piece gutta percha core/cone 10, in combination with an appropriate luting agent 8, properly seals, in a three dimensional manner, a preparation space of root canal 2 of tooth 5, as well as lateral canals 7 extending therefrom. These lateral canals 7 are more effectively filled with sealers 8 that exhibit little or no shrinkage, rather than thermoplastic obturation techniques that produce shrinkage upon cooling. These sealers 8, such as methylacrylates, expand slightly rather than shrink, and fill lateral canals 7 of root canal 2 more successfully than thermoplastic gutta percha.

OPERATION S AND BENEFITS OF THE INVENTION

The gutta percha core/cone technique is an advance in Endodontics that facilitates the obturation of the root canal space for all clinicians. The synchronicity developed between a machined fully tapered 0.03 to 0.08 preparation of a root canal 2, preferably a 0.04 or 0.06 preparation, and the precise match of the appropriate gutta percha core/cone 10 allows the dentist to achieve a precision fit in Endodontics, much like a precision fit in industry. As a result of this technique, clinicians can now not only fill a root canal 2 faster (thereby saving the patient time) but also they can fill it better in a true three dimensional sense. Because the fit is precise, the cement layer of luting agent sealer 8 between the gutta percha core/cone 10 and the tooth structure l(inside walls of the root canal 2) is very thin. A thin cement layer of luting agent sealer 8 is far less prone to shrinkage as compared to heated gutta percha, which shrinks significantly upon cooling. Additionally, when the interior of the root canal is properly conditioned with a chelating agent, such as ETDA, the dentinal tubules and lateral canals are opened sufficiently to allow the sealer (luting agent) to fill the spaces. The result is a better bond (retention) between the gutta percha and the dentinal wall, as well as more effective obturation of the lateral canals. Consequently, the goal of a true hermetic seal is closer to being achieved with the gutta percha core/cone technique than any other prior art methods.

The unique design features of the gutta percha core/cone 10, along with the characteristics achieved by optionally having the core/cone 10 undergo cryogenic treatment, render multiple advantages to this technique.

The handle design of the core/cone 10 is unique and its design allows for ease of placement of the integral one piece gutta percha core/cone 10 into the prepared root canal 2 of a tooth 1. The handle 12 is also made of the same gutta percha material (which is identical to the rest of the core/cone 10) and therefore no separate solid core with a wrap of possibly precariously adhesable gutta percha is needed. This is important due to the viscosity of the sealer.

The texturized reticulated surface area 20, (such as, for example, a lattice framework or other dimpled texturization and the like) increases surface area and provides greater retention of the luting agent sealer 8, such as cement, to the core/cone 10. This unique feature enhances bonding between the luting agent sealer 8 (such as cement) and the core/cone 10 along with forming mechanical locks.

The preferably optional cryogenic treatment of the core/cone material (gutta percha) creates advantages previously unseen with gutta percha. By making the gutta percha stiffer, the cryogenic treatment allows the gutta percha core/cone 10 to work better with the viscosity of sealers (cements) associated with this technique. Stiffer gutta percha can be pre-curved into a one-piece integral gutta percha core/cone 10 without the need for a separate stiffer carrier core, and this feature will facilitate the "obturation" of more challenging root canal anatomy. Stiffer gutta percha is also easier for the clinician to handle, as well as to insert into the root canal space, thereby maintaining the integrity of the gutta percha core/cone 10.

Optional length markings 14 on the gutta percha core/cone 10 itself will facilitate accurate placement of the core/cone 10 into a canal 2, and will help ensure the success of the procedure. The packaging of each core/cone 10 in its own separate wrapper 6 will help reduce bacterial contamination during the process of obturation of a root canal space 2. As a result of this aseptic technique, the obturation process has a better prognosis.

It is further known that other embodiments may be made to the present invention, within the scope of the invention, as noted in the Claims.

We claim:

1. An endodontic integral one piece gutta percha core/cone adapted to remain in and seal a root canal comprising:

a) a handle portion at a proximal end of said endodontic integral one piece core/cone made from gutta percha and adapted to be gripped by a delivery vehicle clasp;

b) a length determination section adjoining said handle portion having depth markings to indicate when the endodontic integral one piece core/cone is fully inserted into a root canal; and c) a conical section adjacent to said length determination section terminating in a tip having a predetermined size at the distal end of said endodontic integral one piece core/cone, said conical section being reticulated to increase surface area and adapted to fill said root canal.

2. The endodontic integral one piece gutta percha core/cone of claim 1 in which said endodontic integral one piece gutta percha core/cone is cryogenically deep frozen.

3. The endodontic integral one piece gutta percha core/cone of claim 1 having a luting agent coating the surface area of said conical section.

4. The endodontic integral one piece gutta percha core/cone of claim 3 in which said luting agent is a glass ionomer.

5. The gutta percha core/cone as in claim 4 wherein said glass ionomer is poly alkenoate acid glass ionomer cement.

6. The gutta percha core/cone as in claim 5 wherein said cement is resin modified.

7. The gutta percha core/cone as in claim 5 wherein said cement is a poly methyl methacrylate.

8. The gutta percha core/cone as in claim 7 wherein said methyl methacrylate is urethane dimethacrylate (UDMA).

9. The gutta percha core/cone as in claim 7 wherein said methyl methacrylate is bisglycidyl methacrylate (BIS-GMA).

10. The endodontic integral one piece gutta percha core/cone of claim 5 in which said thin layer of a luting agent coating is resin.

11. The endodontic integral one piece gutta percha core/cone of claim 5 in which said luting agent coating is a sealer.

12. The endodontic integral one piece gutta percha core/cone of claim 3 in which said luting agent coating is a siloxane.

13. The endodontic integral one piece gutta percha core/cone of claim 1 in which said depth markings on said length determination section are made up of thick lines to denote odd lengths and thin lines to denote even lengths.

14. The endoclontic integral one piece gutta percha core/cone of claim 1 in which said depth markings on said length determination section are made up of thick lines to denote even lengths and thin lines to denote odd lengths.

15. The endodontic integral one piece gutta percha core/cone of claim 1 sized to fit a particular machined root canal space.

16. The endodontic integral one piece gutta percha core/cone of claim 15 in which the conical section has a taper selected in the range of 0.03 millimeter (mm) to 0.08 millimeter (mm) per each lengthwise millimeter (mm) measured one millimeter (mm) up from a distal tip of said integral one piece gutta percha core/cone.

17. The endodontic integral one piece gutta percha core/cone of claim 15 in which the conical section has a taper selected in the range of 0.04 millimeter (mm) to 0.06 millimeter (mm) per each lengthwise millimeter (mm) measured one millimeter (mm) up from a distal tip of said integral one piece gutta percha core/cone.

18. The endodontic integral one piece gutta percha core/cone of claim 1 individually packaged in a seal.

19. The endodontic integral one piece gutta percha core/cone of claim 1 wherein said integral one piece gutta percha core/cone is provided in a set of core/cones with constant tip size and variable tapers.

20. The endodontic integral one piece gutta percha core/cone of claim 1 wherein said integral one piece gutta percha core/cone is provided in a set of core/cones with variable tip sizes and constant taper.

21. An endodontic integral one piece gutta percha core/cone capable of sealing a root canal preparation area comprising:

a) a handle portion at a proximal end of said endodontic integral one piece core/cone made from gutta percha and adapted to be gripped by a delivery vehicle clasp:

b) a length determination section adjoining said handle portion having depth markings to indicate when the endodontic integral one piece core/cone is fully inserted into a root canal;

c) a conical section adjacent said length determination section terminating in a point at the distal end of said endodontic integral one piece core/cone, said conical section being reticulated to increase surface area and adapted to fill said root canal, said endodontic integral one piece gutta percha core/cone being cryogenically deep frozen; and d) a thin layer of a luting agent coating the surface area of said conical section and reducing shrinkage thereof.

22. The endodontic integral one piece gutta percha core/cone of claim 21 in which said thin layer of a luting agent coating is a cement.

23. The endodontic integral one piece gutta percha core/cone of claim 22 wherein said integral one piece gutta percha core/cone is provided in a set of core/cones with variable tip sizes and constant taper.

24. The endodontic integral one piece gutta percha core/cone of claim 21 in which said thin layer of a luting agent coating is a glass ionomer.

25. The gutta percha core/cone as in claim 24 wherein said glass ionomer cement is poly alkenoate acid glass ionomer cement.

26. The gutta percha core/cone as in claim 24 wherein said cement is resin modified.

27. The gutta percha core/cone as in claim 24 wherein said cement is a poly methyl methacrylate.

28. The gutta percha core/cone as in claim 24 wherein said methyl methacrylate is urethane dimethacrylate (UDMA).

29. The gutta percha core/cone as in claim 24 wherein said methyl methacrylate is-bisglycidyl-methacrylate (BIS-GMA).

30. The endodontic integral one piece gutta percha core/cone of claim 21 in which said thin layer of a luting agent coating is resin.

31. The endodontic integral one piece gutta percha core/cone of claim 21 in which said thin layer of a luting agent coating is a sealer.

32. The endodontic integral one piece gutta percha core/cone of claim 21 in which said thin layer of a luting agent coating is a siloxane.

33. The endodontic integral one piece gutta percha core/cone of claim 21 in which said depth markings on said length determination section are made up of thick lines to denote odd lengths and thin lines to denote even lengths.

34. The endodontic integral one piece gutta percha core/cone of claim 21 in which said depth markings on said length determination section are made up of thick lines to denote even lengths and thin lines to denote odd lengths.

35. The endodontic integral one piece gutta percha core/cone of claim 21 sized to fit a particular machined root canal space.

36. The endodontic integral one piece gutta percha core/cone of claim 21 in which the conical section has a taper selected in the range of 0.03 millimeter (mm) to 0.08 millimeter (mm) per each lengthwise millimeter (mm) measured one millimeter (mm) up from a distal tip of said integral one piece gutta percha core/cone.

37. The endodontic integral one piece gutta percha core/cone of claim 36 in which the conical section has a taper selected in the range of 0.04 millimeter (mm) to 0.06 millimeter (mm) per each lengthwise millimeter (mm) measured one millimeter (mm) up from a distal tip of said integral one piece gutta percha core/cone.

38. The endodontic integral one piece gutta percha core/cone of claim 21 individually packaged in a seal.

39. The endodontic integral one piece gutta percha core/cone of claim 21 wherein said integral one piece gutta percha core/cone is provided in a set of core/cones with constant tip size and variable tapers.

40. An endodontic integral one piece gutta percha core/cone capable of sealing a root canal preparation area comprising: a conical section being reticulated to increase surface area and adapted to fill said root canal, said endodontic integral one piece gutta percha core/cone being cryogenically deep frozen.

41. The endodontic integral one piece gutta percha core/cone as in claim 40, further comprising a handle portion at a proximal end of said endodontic integral one piece gutta percha core/cone made from gutta percha and adapted to be gripped by a delivery vehicle clasp.

42. The endodontic integral one piece gutta percha core/cone of claim 41 further comprising a length determination section adjoining said handle portion having depth markings to indicate when the endodontic integral one piece core/cone is fully inserted into a root canal.

43. The endodontic integral one piece gutta percha core/cone of claim 42 in which said depth markings on said length determination section are made up of thick lines to denote odd lengths and thin lines to denote even lengths.

44. The endodontic integral one piece gutta percha core/cone of claim 42 in which said depth markings on said length determination section are made up of thick lines to denote even lengths and thin lines to denote odd lengths.

45. The endodontic integral one piece gutta percha core/cone of claim 40 further comprising a thin layer of a luting agent coating the surface area of said conical section and reducing shrinkage thereof.

46. The endodontic integral one piece gutta percha core/cone of claim 43 in which said thin layer of a luting agent coating is resin.

47. The endodontic integral one piece gutta percha core/cone of claim 43 in which said thin layer of a luting agent coating is a sealer.

48. The endodontic integral one piece gutta percha core/cone of claim 43 in which said thin layer of a luting agent coating is a siloxane.

49. The endodontic integral one piece gutta percha core/cone of claim 40 in which said thin layer of a luting agent coating is a cement.

50. The endodontic integral one piece gutta percha core/cone of claim 40 in which said thin layer of a luting agent coating is a glass ionomer.

51. The gutta percha core/cone as in claim 50 wherein said glass ionomer cement is poly alkenoate acid glass ionomer cement.

52. The gutta percha core/cone as in claim 50 wherein said cement is resin modified.

53. The gutta percha core/cone as in claim 50 wherein said cement is a poly methyl methacrylate.

54. The gutta percha core/cone as in claim 50 herein said methyl methacrylate is UDMA—urethane dimethacrylate.

55. The gutta percha core/cone as in claim 50 wherein said methyl methacrylate is bisglycidyl methacrylate (BIS-GMA).

56. The endodontic integral one piece gutta percha core/cone of claim 40 sized to fit a particular machined root canal space.

57. The endodontic integral one piece gutta percha core/cone of claim 40 in which the conical section has a taper selected in the range of 0.03 millimeter (mm) to 0.08 millimeter (mm) per each lengthwise millimeter (mm) measured one millimeter (mm) up from a distal tip of said integral one piece gutta percha core/cone.

58. The endodontic integral one piece gutta percha core/cone of claim 40 in which the conical section has a taper selected in the range of 0.04 millimeter (mm) to 0.06 millimeter (mm) per each lengthwise millimeter (mm) measured one millimeter (mm) up from a distal tip off said integral one piece gutta percha core/cone.

59. The endodontic integral one piece gutta percha core/cone of claim 40 individually packaged in a seal.

60. The endodontic integral one piece gutta percha core/cone of claim 40 wherein said integral one piece gutta percha core/cone is provided in a set of core/cones with constant tip size and variable tapers.

61. The endodontic integral one piece gutta percha core/cone of claim 40 wherein said integral one piece gutta percha core/cone is provided in a set of core/cones with variable tip sizes and constant taper.

62. An endodontic integral one piece gutta percha core/cone comprising surface treated gutta percha, wherein said gutta percha is coated with a coupling agent.

63. The gutta percha core/cone as in claim 62 wherein said coupling agent is an organosilane.

64. The gutta percha core/cone as in claim 62 wherein said coupling agent is an 3-methoxy-propyl-trimethoxy-silane.

65. The gutta percha core/cone as in claim 62 further comprising a chemical sealer.

66. The gutta percha core/cone as in claim 62 further comprising a sealer comprising a glass ionomer cement.

67. The gutta percha core/cone as in claim 66 wherein said glass ionomer cement is poly alkenoate acid glass ionomer cement.

68. The gutta percha core/cone as in claim 62 wherein said cement is resin modified.

69. The gutta percha core/cone as in claim 62 wherein said cement is a poly methyl methacrylate.

70. The gutta percha core/cone as in claim 69 wherein said methyl methacrylate is urethane dimethacrylate (UDMA).

71. The gutta percha core/cone as in claim 69 wherein said methyl methacrylate is bisglycidyl methacrylate (BIS-GMA).

72. The endodontic integral one piece gutta percha core/cone as in claim 62, further comprising a handle portion at a proximal end of said endodontic integral one piece gutta percha core/cone made from gutta percha and adapted to be gripped by a delivery vehicle clasp.

73. The endodontic integral one piece gutta percha core/cone of claim 62 further comprising a length determination section adjoining said handle portion having depth markings to indicate when the endodontic integral one piece core/cone is fully inserted into a root canal.

74. A synchronistic method of filling and sealing a root canal comprising the steps of: a) measuring the depth of said root canal from a reference point to the apex of said canal; b) selecting a endodontic integral one piece core/cone made of gutta percha properly sized for said root canal, said endodontic integral one piece core/cone comprising a handle portion at a proximal end of said endodontic integral one piece core/cone made from gutta percha and adapted to be gripped by a delivery vehicle clasp, a length determination section adjoining said handle portion having depth markings to indicate when the endodontic integral one piece core/cone is fully inserted into a root canal, a conical section adjacent said length determination section terminating in a point at the distal end of said endodontic integral one piece core/cone, said conical section being reticulated to increase surface area and adapted to fill said root canal; c) coating the conical section of said core with a thin layer of a luting agent; d) coating the inside of said root canal with said luting agent; e) inserting said endodontic integral one piece gutta percha core/cone into said root canal as far as the appropriate depth marking; and f) after a sufficient length of time for the cement coatings to bone, severing the endodontic integral one piece core/cone at the orifice of the canal.

75. The method of claim 74 in which said luting agent coating is a cement.

76. The method of claim 74 in which said luting agent coating is a glass ionomer.

77. The method of claim 74 in which said luting agent coating is resin.

78. The method of claim 74 in which said luting agent coating is a sealer.

79. The method of claim 74 in which said luting agent coating is a siloxane.

80. The method of claim 74 in which the handle section of said endodontic integral one piece core/cone is grasped by a delivery vehicle clasp to manipulate said endodontic integral one piece core/cone into said root canal.

81. The method of claim 74 in which said endodontic integral one piece core/cone is cryogenically frozen before coating with cement.

82. An endodontic integral one piece gutta percha core/cone capable of sealing a root canal preparation area comprising:
  a) a handle portion at a proximal end of said endodontic integral one piece core/cone made from gutta percha and adapted to be gripped by a delivery vehicle clasp;
  b) a uniformly tapered conical section adjacent to a length determination section terminating in a point at the distal end of said endodontic integral one piece core/cone; and,
  c) said conical section having reticulations to increase surface area and adapted to fill, seal and remain in said root canal preparation area.

83. The endodontic integral one piece gutta percha core/cone of claim 82 further comprising a length determination section adjoining said handle portion having depth markings to indicate when the endodontic integral one piece core/cone is fully inserted into a root canal.

84. The endodontic integral one piece gutta percha core/cone of claim 83 in which said depth markings on said length determination section are made up of thick lines to denote odd lengths and thin lines to denote even lengths.

85. The endodontic integral one piece gutta percha core/cone of claim 83 in which said depth markings on said length determination section are made up of thick lines to denote even lengths and thin lines to denote odd lengths.

86. The endodontic integral one piece gutta percha core/cone of claim 82, in which the cone/cone is custom fit.

87. The endodontic integral one piece gutta percha core/cone of claim 82 individually packaged in a seal.

88. The endodontic integral one piece gutta percha core/cone of claim 82 wherein said integral one piece gutta percha core/cone is provided in a set of core/cones with constant tip size and variable tapers.

89. The endodontic integral one piece gutta percha core/cone of claim 82 wherein said integral one piece gutta percha core/cone is provided in a set of core/cones with variable tip sizes and constant taper.

90. The endodontic integral one piece gutta percha core/cone of claim 82 in which the conical section has a taper selected in the range of 0.03 millimeter (mm) to 0.08 millimeter (mm) per each lengthwise millimeter (mm) measured one millimeter (mm) up from a distal tip of said integral one piece gutta percha core/cone.

91. The endodontic integral one piece gutta percha core/cone of claim 90, in which the conical section has a taper selected in the range of 0.04 millimeter (mm) to 0.06 millimeter (mm) per each lengthwise millimeter (mm) measured one millimeter (mm) up from a distal tip of said integral one piece gutta percha core/cone.

92. The endodontic integral one piece gutta percha core/cone of claim 82, in which said endodontic integral one piece gutta percha core/cone is cryogenically deep frozen.

93. The endodontic integral one piece gutta percha core/cone of claim 82, further comprising a thin layer of a luting agent coating the surface area of said conical section and reducing shrinkage thereof.

94. The endodontic integral one piece gutta percha core/cone of claim 93, in which said thin layer of a luting agent coating is a cement.

95. The endodontic integral one piece gutta percha core/cone of claim 93, in which said thin layer of a luting agent coating is resin.

96. The endodontic integral one piece gutta percha core/cone of claim 93, in which said thin layer of a luting agent coating is a sealer.

97. The endodontic integral one piece gutta percha core/cone of claim 93, in which said thin layer of a luting agent coating is a siloxane.

98. The endodontic integral one piece gutta percha core/cone of claim 93, in which said thin layer of a luting agent coating is a glass ionomer.

99. The gutta percha core/cone as in claim 98, wherein said glass ionomer cement is poly alkenoate acid glass ionomer cement.

100. The gutta percha core/cone as in claim 99, wherein said cement is a poly methyl methacrylate.

101. The gutta percha core/cone as in claim 100, wherein said poly methyl methacrylate is UDMA—urethane dimethacrylate.

102. The gutta percha core/cone as in claim 100, wherein said poly methyl methacrylate is BIS-GMA—bisglycidyl methacrylate.

103. The gutta percha core/cone as in claim 98, wherein said cement is resin modified.

* * * * *